United States Patent [19]

Ono et al.

[11] Patent Number: 5,032,636
[45] Date of Patent: Jul. 16, 1991

[54] ORGANOSILICON COMPOUND

[75] Inventors: Ichiro Ono, Annaka; Hiroshi Yoshioka, Tokyo, both of Japan

[73] Assignee: Shin-Etsu Chemical Co., Ltd., Tokyo, Japan

[21] Appl. No.: 480,329

[22] Filed: Feb. 13, 1990

Related U.S. Application Data

[63] Continuation of Ser. No. 306,205, Feb. 2, 1989, abandoned, which is a continuation of Ser. No. 216,115, Jul. 7, 1988, abandoned.

[30] Foreign Application Priority Data

Jul. 17, 1987 [JP] Japan .................. 62-178593

[51] Int. Cl.$^5$ .............................................. C08K 5/54
[52] U.S. Cl. ....................... 524/265; 524/269; 524/267; 524/555; 524/567; 524/565; 524/575; 524/577; 524/579; 524/582; 524/585
[58] Field of Search .................. 524/267, 269, 265

[56] References Cited

U.S. PATENT DOCUMENTS 4,134,906 1/1979 Oswald et al. .................. 556/10

FOREIGN PATENT DOCUMENTS 621459 6/1961 Canada .................. 556/435
59-025310 2/1984 Japan .................. 556/435

OTHER PUBLICATIONS

Chem. Abstracts, vol. 84:105685q, Stepwise Addition of Silanes & Phosphines to $\alpha$, $\omega$ Dienes, 1975.

*Primary Examiner*—Joseph L. Schofer
*Assistant Examiner*—Mark D. Sweet
*Attorney, Agent, or Firm*—Wyatt, Gerber, Burke and Badie

[57] ABSTRACT

Organosilicon compounds of a novel class are disclosed including $\alpha,\omega$-bis(alkoxy silyl)-substituted alkane compounds represented by the general formula

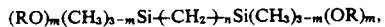

$$(RO)_m(CH_3)_{3-m}Si\text{-}(CH_2)_n\text{-}Si(CH_3)_{3-m}(OR)_m,$$

in which R is a monovalent hydrocarbon group having 1 to 4 carbon atoms, e.g., methyl and ethyl, the subscript n is a positive integer in the range from 10 to 18 and the subscript m is 1, 2 or 3. The compound is useful as an additive in various kinds of synthetic resin-based compositions for the purpose of improving the properties such as flexibility, weatherability, cold resistance and mechanical strengths.

3 Claims, No Drawings

ORGANOSILICON COMPOUND

This is a continuation of application Ser. No. 07/306,205 filed Feb. 2, 1989 now abandoned, which is a continuation of Ser. No. 07/216,115, filed Jul. 7, 1988 now abandoned.

BACKGROUND OF THE INVENTION

The present invention relates to a novel organosilicon compound not known in the prior art nor described in any publications. The compound has been unexpectedly discovered in the course of the investigations to obtain an efficient additive compound for improving shaped articles of various kinds of synthetic resins relative to flexibility, weatherability, cold resistance, curability and mechanical strengths. Related disclosures are found in U.S. Pat. No. 4,268,682 and in Kogakubu Kenkyu Hokoku, Chiba University, Japan, vol. 37, No. 2, pages 35–40 (1986) (Kojima et al.).

SUMMARY OF THE INVENTION

The novel organosilicon compound provided by the present invention is an $\alpha,\omega$-bis(alkoxysilyl)-substituted polymethylene compound represented by the general formula $$(RO)_m(CH_3)_{3-m}Si-(CH_2)_n-Si(CH_3)_{3-m}(OR)_m, \quad (I)$$

in which R is a monovalent hydrocarbon group having 1 to 4 carbon atoms selected from alkyl and alkenyl groups, the subscript n is a positive integer of, for example, 10 to 18 and the subscript m is 1, 2 or 3. Preferably, the group denoted by R is a methyl or an ethyl group when the compound is intended to be an additive in synthetic resins in respect of the reactivity.

DETAILED DESCRIPTION OF THE PREFERRED EMBODIMENTS

The $\alpha,\omega$-bis(alkoxysilyl)-substituted polymethylene compound as the novel compound of the invention is represented by the above given general formula (I). The group denoted by R is an aliphatic monovalent hydrocarbon group exemplified by alkyl groups such as methyl, ethyl, propyl and butyl groups and alkenyl groups such as vinyl, allyl and butenyl groups. When the compound is used as an additive in synthetic resin compositions, the group denoted by R is preferably a methyl or an ethyl group in respect of the reactivity. The subscript m is 1, 2 or 3 and the subscript n is a positive integer. When the compound is used as an additive in synthetic resin compositions, the subscript n is preferably a positive integer in the range from 10 to 18 though not particularly limitative thereto in view of the compatibility of the compound with the synthetic resin.

Examples of the inventive $\alpha,\omega$-bis(alkoxysilyl)-substituted polymethylene compounds include those expressed by the following structural formulas, in which the symbols Me and Et denote a methyl and an ethyl group, respectively:

$(MeO)Me_2Si-(CH_2)_{10}-SiMe_2(OMe)$;

$(EtO)_2MeSi-(CH_2)_{10}-SiMe(OEt)_2$;

$(MeO)_3Si-(CH_2)_{10}Si(OMe)_3$;

$(EtO)_3Si-(CH_2)_{10}Si(OEt)_3$;

$(EtO)_2MeSi-(CH_2)_{10}SiMe(OEt)_2$;

$(EtO)_3Si-(CH_2)_{12}Si(OEt)_3$;

$(MeO)_3Si-(CH_2)_{14}Si(OMe)_3$;

$(MeO)_2MeSi-(CH_2)_{14}-SiMe(OMe)_2$;

$(MeO)_3Si-(CH_2)_{18}Si(OMe)_3$; and $(EtO)_2MeSi-(CH_2)_{18}SiMe(OEt)_2$.

These organosilicon compounds can be synthesized by a variety of synthetic routes. A convenient and efficient route for the synthesis of these compounds is as follows. In the first place, namely, two moles of a mono-, di- or trialkoxy hydrogen silane compound represented by the general formula $$(RO)_mMe_{3-m}SiH,$$

in which each symbol has the same meaning as defined above, is reacted with one mole of an $\alpha,\omega$-divinyl polymethylene compound represented by the general formula $$CH_2=CH-(CH_2)_{n-4}-CH=CH_2,$$

in which the subscript n has the same meaning as defined above, in the presence of a catalytic amount of a platinum compound as a catalyst for promoting the addition reaction between the silicon-bonded hydrogen atoms in the mono-, di- or trialkoxy hydrogen silane compound and the terminal vinyl groups in the $\alpha,\omega$-divinyl polymethylene compound.

Alternatively, two moles of a mono-, di- or trihalogeno hydrogen, silane compound represented by the general formula $$X_mMe_{3-m}SiH,$$

in which X is an atom of halogen, e.g., chlorine, and m has the same meaning as defined above, is reacted with one mole of an $\alpha,\omega$-divinyl polymethylene compound represented by the general formula $$CH_2=CH-(CH_2)_{n-4}-CH=CH_2,$$

in which the subscript n has the same meaning as defined above, in the presence of a platinum catalyst to give an $\alpha,\omega$-bis(chlorosilyl)-substituted polymethylene compound represented by the general formula $$X_m(CH_3)_{3-m}Si-(CH_2)_n-Si(CH_3)_{3-m}X_m,$$

which is then reacted with an alcohol represented by the general formula ROH, in which R has the same meaning as defined above, to give the desired inventive compound of the general formula (I) by the dehydrohalogenation reaction.

The $\alpha,\omega$-bis(alkoxysilyl)-substituted polymethylene compound of the invention represented by the above given general formula (I) is a novel compound not known in the prior art nor described in any publications. This compound can be used in various applications, of which the most promising application is as an additive to various kinds of synthetic resins for improving shaped articles of the synthetic resins relative to flexibility, weatherability, cold resistance, curability, mechanical strengths and other properties. The type of the synthetic resin, of which the properties of the shaped articles can be improved by the addition of the inventive organosilicon compound, is not particularly limitative including many of known synthetic resins. In particular, examples of synthetic resins of which remarkable improvements can be obtained by the addition of the inventive compound include polyolefin resins such as polyethylene and polypropylene, polyvinyl chloride resins as well as copolymeric resins of vinyl chloride and vinyl acetate, polystrenes, ABS resins, AS resins, SB resins, polymethyl methacrylate resins, saturated polyester resins, polyamide resins, polyurethane resins, epoxy resins, phenolic resins, amino resins, polycarbonate resins, fluorocarbon resins, cellulosic resins, polybutadiene resins, alkyd resins, melamine resins and the like. In addition, the inventive organosilicon compound can be used as an additive for improving the properties of various kinds of modified silicone resins obtained by modifying a silicone resin, e.g., methyl silicones and methyl phenyl silicones, with other organic resins such as acrylic resins, polyester resins, epoxy resins, urethane resins, phenolic resins, alkyd resins and the like.

In the following, the novel organosilicon compound of the invention is described by way of synthetic examples, in which the compounds were synthesized and characterized, and application examples, in which the compounds were used as an additive in coating compositions and shaped articles of synthetic resins. The term of "parts" in the following examples always refers to "parts by weight". In the application examples described below, the properties of the shaped articles or coating films of synthetic resins were evaluated in terms of several items of which the procedures for the measurement were as follows.

Pencil Hardness Test

Measurement was performed according to the procedure of the "pencil scratching test" specified in JIS K 5400, Article 6.14.

Checkerboard Test for Adhesion

According to the procedure of the "checkerboard test" specified in JIS K 5400, Article 6.15, the coating film on a substrate was cut across and down to make six incision lines of 2 mm intervals in each direction with a knife edge so as to form 25 checkerboard squares and then a cellophane-based pressure-sensitive adhesive tape was applied to the checkerboard area of the coating film and forcibly peeled off therefrom to count the number of the checkerboard squares left unlifted on the substrate surface.

Flexibility Test

According to the procedure of the "flexibility test" specified in JIS K 5400, Article 6.16, a test panel coated with the coating film was bent by 180° around a mandrel of 2 mm diameter to examine the condition of the coating film.

Accelerated Weathering Test

The shaped article was subjected to accelerated weathering under irradiation with ultraviolet light repeating the cycles each composed of 2 hours of exposure at 170° C. under a dry condition and 4 hours of exposure at 50° C. under a wet condition over a period of 1000 hours to visually examine the outer appearance of the shaped article.

Heat Cycle Test

Ten pieces of shaped articles were subjected to repeated cycles of heating and quenching each composed of 2 minutes of a heating stage by dipping in a silicone oil bath at 150° C. and 2 minutes of a quenching stage by dipping in liquid nitrogen and the number of repeated cycles was recorded until cracks were found on at least one of the shaped articles.

Scratch Resistance Test

The surface coated with the coating composition was forcibly rubbed by using a lump of steel wool to be examined for the appearance of scratches to record the results in two ratings of A for complete absence of scratches even by forcible rubbing and B for appearance of scratches more or less by forcible rubbing.

Thermal Stability Test

The test specimens were heated at 80° C. for 16 hours and the surface thereof was visually examined for the appearance of cracks.

Heat-shock Resistance test

The test specimens were subjected to six times repeated cycles of heating and quenching each composed of a cold stage at $-30°$ C. for 30 minutes and a hot stage at 100° C. for 30 minutes and the surface thereof was visually examined for the appearance of cracks.

SYNTHETIC EXAMPLE 1

Into a glass-made flask of 1 liter capacity equipped with a stirred, thermometer, reflux condenser and dropping funnel were introduced 207 g (1.5 moles) of 1,9-decadiene and 1.47 g of a solution of chloroplatinic acid in isobutyl alcohol in a concentration of 2% by weight as platinum to form a reaction mixture, into which 402.6 g (3.3 moles) of trimethoxy silane were added dropwise with agitation at 60° C. Evolution of heat was noted in the reaction mixture as the trimethoxy silane was added thereto so that the flask was cooled from outside to keep the temperature at or below 90° C. Agitation of the reaction mixture was continued for additional two hours after completion of the dropwise addition of the trimethoxy silane by keeping the temperature of the mixture at about 90° C. After completion of the reaction, the reaction mixture was distilled to give 519.1 g of a colorless and clear liquid boiling at 170° to 175° C. under a pressure of 3 mmHg as a product.

This liquid product has a viscosity of 6.60 centistokes at 25° C., specific gravity of 0.990 and refractive index of 1.4275 and could be identified to be 1,10-bis(trimethoxysilyl) decane of the formula $(CH_3O)_3Si$-$(CH_2)_{10}$-$Si(OCH_3)_3$ from the results of the elementary analysis, infrared absorption spectrophotometric analysis and nuclear magnetic resonance spectrometric analysis shown below. This product is referred to as the bissilyl alkane I hereinbelow.

| [Elementary analysis] | | | |
| --- | --- | --- | --- |
| | C | H | Si |
| Calculated, %, for $C_{16}H_{38}O_6Si_2$ | 50.22 | 10.01 | 14.68 |
| Found, % | 50.35 | 10.20 | 14.47 |

Infrared absorption spectrum: 810 cm$^{-1}$: Si—C, 1085 cm$^{-1}$ and 1190 cm$^{-1}$: C—O—Si.

Nuclear magnetic resonance spectrum ($\delta$, ppm) 0.87 (t, 4H): Si—CH$_2$, 1.34 to 1.94 (m, 16H): C—CH$_2$—C, 3.83 (s, 18H): O—CH$_3$.

SYNTHETIC EXAMPLE 2

The experimental procedure was substantially the same as in Synthetic Example 1 except that 207 g of 1,9-decadiene were replaced with 375 g (1.5 moles) of 1,17-octadecadiene and the reaction mixture after completion of the reaction was subjected to stripping of low-boiling matters at 200° C. under a pressure of 3 mmHg to give 632.8 g of a clear, light yellow liquid as a product. This liquid product could be identified to be 1,18-bis(trimethoxysilyl) octadecane of the formula $(CH_3O)_3Si-(CH_2)_{18}Si(OCH_3)_3$ from the results of the elementary analysis, infrared absorption spectrophotometric analysis and nuclear magnetic resonance spectrometric analysis shown below. This product is referred to as the bissilyl alkane II hereinbelow.

| [Elementary analysis] | C | H | Si |
|---|---|---|---|
| Calculated, %, for $C_{24}H_{54}O_6Si_2$ | 58.25 | 11.00 | 11.35 |
| Found, % | 58.33 | 11.02 | 11.31 |

Infrared absorption spectrum: 810 cm$^{-1}$: Si—C, 1085 cm$^{-1}$ and 1190 cm$^{-1}$: C—O—Si.

Nuclear magnetic resonance spectrum ($\delta$, ppm) 0.87 (t, 4H): Si—CH$_2$, 1.34 to 1.94 (m, 16H): C—CH$_2$—C, 3.83 (s, 18H): O—CH$_3$.

SYNTHETIC EXAMPLE 3

The procedure was substantially the same as in Synthetic Example 1 described above except that 402.6 g of trimethoxy silane were replaced with 541.2 g (3.3 moles) of triethoxy silane to give 494.0 g of a colorless and clear liquid boiling at 201° to 207° C. under a pressure of 1 mmHg. This liquid product could be identified to be 1,10-bis(triethoxysilyl) decane of the formula $(C_2H_5O)_3Si-(CH_2)_{10}Si(OC_2H_5)_3$ from the results of the elementary analysis, infrared absorption spectrophotometric analysis and nuclear magnetic resonance spectrometric analysis shown below. This product is referred to as the bissilyl alkane III hereinbelow.

| [Elementary analysis] | C | H | Si |
|---|---|---|---|
| Calculated, %, for $C_{22}H_{50}O_6Si_2$ | 56.61 | 10.80 | 12.03 |
| Found, % | 56.63 | 10.77 | 11.98 |

Infrared absorption spectrum: 810 cm$^{-1}$: Si—C, 1085 cm$^{-1}$ and 1190 cm$^{-1}$: C—O—Si.

Nuclear magnetic resonance spectrum ($\delta$, ppm) 0.87 (t, 4H): Si—CH$_2$, 1.02 (m, 18H): O—CH$_2$—C$\underline{H}_3$, 1.30 to 1.89 (m, 16H): C—CH$_2$—C, 3.86 (q, 12H): O—C$\underline{H}_2$—CH$_3$.

SYNTHETIC EXAMPLE 4

The procedure was substantially the same as in Synthetic Example 1 described above except that 402.6 g of trimethoxy silane were replaced with 349.8 g (3.3 moles) of methyl dimethoxy silane to give 475.3 g of a colorless and clear liquid boiling at 162° to 165° C. under a pressure of 3 mmHg. This liquid product could be identified to be 1,10-bis(methyl dimethoxy silyl) decane of the formula $(CH_3O)_2CH_3Si-(CH_2)_{10}SiCH_3(OCH_3)_2$ from the results of the elementary analysis, infrared absorption spectrophotometric analysis and nuclear magnetic resonance spectrometric analysis shown below. This product is referred to as the bissilyl alkane IV hereinbelow.

| [Elementary analysis] | C | H | Si |
|---|---|---|---|
| Calculated, %, for $C_{16}H_{38}O_4Si_2$ | 54.81 | 10.92 | 16.02 |
| Found, % | 54.85 | 10.95 | 15.97 |

Infrared absorption spectrum: 810 cm$^{-1}$: Si—C, 1085 cm$^{-1}$ and 1190 cm$^{-1}$: C—O—Si.

Nuclear magnetic resonance spectrum ($\delta$, ppm) 0.07 (s, 6H): Si—CH$_3$, 0.86 (t, 4H): Si—CH$_2$, 1.31 to 1.92 (m, 16H): C—CH$_2$—C, 3.83 (s, 18H): O—CH$_3$.

SYNTHETIC EXAMPLE 5

The procedure was substantially the same as in Synthetic Example 1 described above except that 402.6 g of trimethoxy silane were replaced with 297 g (3.3 moles) of dimethyl methoxy silane to give 356.2 g of a colorless and clear liquid boiling at 155° to 157° C. under a pressure of 3 mmHg. This liquid product could be identified to be 1,10-bis(dimethyl methoxy silyl) decane of the formula $(CH_3O)(CH_3)_2Si-(CH_2)_{10}Si(CH_3)_2(OCH_3)$ from the results of the elementary analysis, infrared absorption spectrophotometric analysis and nuclear magnetic resonance spectrometric analysis shown below. This product is referred to as the bissilyl alkane V hereinbelow.

| [Elementary analysis] | C | H | Si |
|---|---|---|---|
| Calculated, %, for $C_{16}H_{38}O_2Si_2$ | 60.31 | 12.02 | 17.63 |
| Found, % | 60.40 | 12.05 | 17.58 |

Infrared absorption spectrum: 810 cm$^{-1}$: Si—C, 1085 cm$^{-1}$ and 1190 cm$^{-1}$: C—O—Si.

Nuclear magnetic resonance spectrum ($\delta$, ppm) 0.07 (s, 12H): Si—CH$_3$, 0.85 (t, 4H): Si—CH$_2$, 1.28 to 1.89 (m, 16H): C—CH$_2$—C, 3.81 (s, 6H): O—CH$_3$.

APPLICATION EXAMPLE 1

A copolymeric resin in the form of a solution containing 49% by weight of solid was prepared by the dropwise addition of a mixture composed of 80 parts of methyl methacrylate, 10 parts of butyl acrylate, 10 parts of 3-methacryloxypropyl trimethoxy silane and 3 parts of azobisisobutyronitrile into 100 parts of toluene at 90° C. and the mixture was heated at the same temperature for 8 hours. The copolymer thus obtained has an average molecular weight of about 10,000 with reference to polystyrenes.

Five coating compositions, referred to as the compositions I to V hereinbelow, were prepared each by uniformly blending 100 parts of the above prepared copolymer, 1 part of dibutyl tin dioctoate and 10 parts of the bissilyl alkane I (Composition I), 20 parts of bissilyl alkane I (Composition II) 10 parts of bissilyl alkane III (Composition III), 10 parts of the bissilyl alkane IV (Composition IV) and 10 parts of the bissilyl alkane II (Composition V), respectively.

For comparison, three more coating compositions, referred to as the compositions V to VIII hereinbelow, were prepared each in the same formulation as in the composition I above excepting omission of the bissilyl alkane I, replacement of the bissilyl alkane I with the same amount of an $\alpha,\omega$-dihydroxy hexaeicosamethyl tridecasiloxane of the formula HO-(SiMe$_2$—O)$_{13}$H and replacement of the bissilyl alkane I with the same amount of 1,2-bis(trimethoxy silyl) ethane, respectively.

Test panels of steel having a thickness of 0.3 mm were coated with one of the above prepared compositions I to VIII by spraying in a coating amount to give a coating film having a thickness of 20 μm as dried and the coating films were cured first by standing at room temperature for 24 hours and then by heating at 120° C. for 30 minutes to give test specimens of which the properties were examined according to the procedures described above to give the results shown in Table 1 below. The test specimen of the coating film prepared by using the composition VII was apparently very poor in the appearance with cissing and orange peel so that the test specimen was omitted from the examination.

TABLE 1

| Composition No. | Pensil hardness | Checkerboard test | Flexibility test | Accelerated weathering test |
|---|---|---|---|---|
| I | 2H | 100/100 | No peeling | Gloss retained |
| II | H | 100/100 | No peeling | Gloss retained |
| III | 2H | 100/100 | No peeling | Gloss retained |
| IV | 2H | 100/100 | No peeling | Gloss retained |
| V | 2H | 100/100 | No peeling | Gloss retained |
| VI | 2H | 0/100 | Peeling allover the surface with cracks | Chalking |
| VIII | 2H | 24/100 | Peeling allover the surface with cracks | Chalking |

APPLICATION EXAMPLE 2

Three epoxy-based molding compounds, referred to as the compositions IX, X and XI hereinbelow, were prepared each by uniformly blending 63 parts of a cresol novolac-type epoxy resin having an epoxy equivalent of 210, 32 parts of a phenol novolac resin having a hydroxyl equivalent of 110, 5 parts of a brominated epoxy resin containing 35% by weight of bromine and having an epoxy equivalent of 280, 270 parts of a powder of fused quartz glass, 1 part of triphenyl phosphine, 1 part of carnauba wax, 1 part of carbon black, 1.2 parts 3-glycidyloxypropyl trimethoxy silane and 5 parts of the bissilyl alkane I, the bissilyl alkane IV or the bissilyl alkane II, respectively, and milling the mixture for 5 minutes on a hot roller mill at 80° C. followed by cooling and pulverization.

Each of the compositions IX, X and XI was shaped by injection molding under conditions including a temperature of the metal mold of 175° C., injection pressure of 70 kg/cm² and molding time of 2 minutes into test pieces of 4 mm × 10 mm × 100 mm of which the flexural modulus was determined to give the results of 1150 kg/mm², 1100 kg/mm² and 1100 kg/mm² for the compositions IX, X and XI, respectively. Further, 14-pin ICs each having a silicon chip of 4.5 mm × 9.0 mm × 0.5 mm dimensions mounted on a frame were prepared by molding with the above prepared compositions IX, X and XI under substantially the same molding conditions as above and subjected to a heat cycle test to give the results of 100 cycles, 90 cycles and 100 cycles for the compositions IX, X and XI, respectively.

For comparison, two more molding compounds, referred to as the compositions XII and XIII hereinbelow, were prepared each in the same formulation as in the composition IX above excepting omission of the bissilyl alkane I or replacement of the bissilyl alkane I with the same amount of 1,2-bis(trimethoxy silyl) ethane, respectively. The results of the flexural modulus measurement and the heat cycle test were 1300 kg/mm² and 1300 kg/mm² and 5 cycles and 20 cycles for the compositions XII and XIII, respectively.

APPLICATION EXAMPLE 3

Two coating compositions, referred to as the compositions XIV and XV hereinbelow, were prepared each in the following procedure. Thus, a mixture composed of 55 parts of methyl trimethoxy silane, 5 parts of the bissilyl alkane I or II, respectively, and 1.6 parts of acetic acid was chilled and kept at a temperature of 0° to 10° C. on an ice water bath under agitation and then 77 parts of an aqueous dispersion of colloidal silica containing 30% by weight of solid (Snowtex 30, a product by Nissan Chemical Co., average particle diameter 5 to 10 μm) were gradually added dropwise thereto. After completion of the dropwise addition of the colloidal silica dispersion, the mixture was further agitated at 10° C. for 4 and a half hours and then admixed with 100 parts of isopropyl alcohol, 2.3 parts of acetic acid and 0.08 part of a polyethylene glycol-polysiloxane copolymer (KP-341, a product by Shin-Etsu Chemical Co.) followed by aging at room temperature for 7 days. For comparison, another coating composition, referred to as the composition XVI hereinbelow, was prepared in the same formulation as above excepting omission of the bissilyl alkane compound and increase of the amount of methyl trimethoxy silane to 60 parts.

A test plate of polymethyl methacrylate resin (Delaglass A, a product by Asahi Chemical Industry Co.) was coated with the coating composition by dipping and then heated at 80° C. for 30 minutes to cure the coating film thereon. The thus prepared test specimens were subjected to the evaluation tests to give the results of: 6H, 5H and 6H in the pencil hardness test; each 100/100 in the checkerboard test for adhesion; each good in the thermal stability test excepting for the composition XVI with cracks formed; each good in the thermal shock test excepting for the composition XVI with cracks formed; and A, B and A in the scratch resistance test, for the compositions XIV, XV and XVI, respectively.

What is claimed is:

1. An improved synthetic resin-based composition, which comprises: a resin selected from the group consisting of polyolefin resins, polyvinyl chloride resins, copolymers of vinyl chloride and vinyl acetate, polystyrene resins, ABS resins, As resins, SB resins, polymethyl methacrylate resins, saturated polyester resins, polyamide resins, polyurethane resins, epoxy resins, phenolic resins, amino resins, polycarbonate resins, fluorocarbon resin, cellulosic resins, polybutadine resins, alkyl resins and melaminic resins; admixed with α,ω-bis (alkoxy silyl)-substituted alkane compound represented by the general formula:

$(RO)_m(CH_3)_{3-m}Si(CH_2)_n Si(CH_3)_{3-m}(OR)_m$ in which R is a monovalent hydrocarbon group having 1 to 4 carbon atoms, the subscript n is a positive integer in the range from 10 to 18 and the subscript m is 1, 2 or 3; wherein the flexibility, weatherability, cold resistance, curability and mechanical strength of said resin are improved compared to said resin which is not admixed with said substituted alkane compound.

2. The improved resin-based composition of claim 1 wherein the group denoted by R is a methyl group or an ethyl group.

3. The improved resin-based composition of claim 1 wherein the subscript m is 2 or 3.

* * * * *